United States Patent
Pastoor et al.

(10) Patent No.: US 10,736,528 B2
(45) Date of Patent: Aug. 11, 2020

(54) DRY ELECTRODE FOR BIO-POTENTIAL AND SKIN IMPEDANCE SENSING AND METHOD OF USE

(71) Applicant: KONINKLIJKE PHILIPS N.V., Eindhoven (NL)

(72) Inventors: Sander Theodoor Pastoor, Vleuten (NL); Lucas Johannes Anna Maria Beckers, Veldhoven (NL); Timon Rutger Grob, Geldrop (NL); Denny Mathew, Eindhoven (NL); Edward Theodorus Maria Berben, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 326 days.

(21) Appl. No.: 15/572,850

(22) PCT Filed: May 17, 2016

(86) PCT No.: PCT/IB2016/052850
§ 371 (c)(1),
(2) Date: Nov. 9, 2017

(87) PCT Pub. No.: WO2016/189422
PCT Pub. Date: Dec. 1, 2016

(65) Prior Publication Data
US 2018/0116546 A1 May 3, 2018

Related U.S. Application Data

(60) Provisional application No. 62/167,384, filed on May 28, 2015.

(51) Int. Cl.
*A61B 5/0408* (2006.01)
*A61B 5/0416* (2006.01)
(Continued)

(52) U.S. Cl.
CPC .......... *A61B 5/0408* (2013.01); *A61B 5/0416* (2013.01); *A61B 5/0478* (2013.01);
(Continued)

(58) Field of Classification Search
CPC ................................ A61B 5/0408; A61N 1/04
See application file for complete search history.

(56) References Cited

U.S. PATENT DOCUMENTS 5,985,990 A  11/1999  Kantner et al.
8,029,431 B2  10/2011  Tononi
(Continued)

FOREIGN PATENT DOCUMENTS

CN  102824168 A  12/2012
WO  1981002097 A1  8/1981
(Continued)

*Primary Examiner* — Lee S Cohen

(57) ABSTRACT

An electrode configured to provide electrical contact with skin of a subject is provided. The electrode includes an electrode body configured to be removably coupled with the skin of the subject and to receive electrical signals from and/or transmit electrical signals to the skin of the subject, and an electrical coupling that facilitates coupling the electrode to an external computing system. The electrode body includes a conductive silicone material configured to enable uptake or diffusion of moisture from the skin of the subject over which the electrode body is disposed; and a detergent configured to facilitate a flow of ions through the conductive silicone material.

21 Claims, 11 Drawing Sheets

(51) Int. Cl.
  *A61B 5/0478* (2006.01)
  *A61B 5/053* (2006.01)
  *A61N 1/04* (2006.01)

(52) U.S. Cl.
  CPC ........ *A61B 5/04087* (2013.01); *A61B 5/0533* (2013.01); *A61N 1/0456* (2013.01); *A61N 1/0496* (2013.01); *A61B 2560/0412* (2013.01); *A61B 2562/0215* (2017.08); *A61B 2562/0217* (2017.08); *A61B 2562/227* (2013.01); *A61N 1/0452* (2013.01)

(56) References Cited

U.S. PATENT DOCUMENTS

| | | | |
|---|---|---|---|
| 8,608,984 B1 * | 12/2013 | Taranekar | A61B 5/0408 252/511 |
| 9,833,607 B2 * | 12/2017 | Crone | A61N 1/0484 |
| 2014/0088397 A1 | 3/2014 | Chon et al. | |
| 2015/0032194 A1 * | 1/2015 | Mergen | A61N 1/05 607/137 |
| 2015/0283265 A1 * | 10/2015 | Peyman | A61K 47/6923 424/491 |
| 2017/0135596 A1 * | 5/2017 | Fan | A61B 5/0478 |

FOREIGN PATENT DOCUMENTS

| | | |
|---|---|---|
| WO | 199724149 A1 | 7/1997 |
| WO | 2007092290 A2 | 8/2007 |
| WO | 2008006219 A1 | 1/2008 |

\* cited by examiner

REGULAR SNAP    SNAP TO MAGNET ADAPTER

DRY ELECTRODE FOR BIO-POTENTIAL AND SKIN IMPEDANCE SENSING AND METHOD OF USE

CROSS-REFERENCE TO PRIOR APPLICATIONS

This application is the U.S. National Phase application under 35 U.S.C. § 371 of International Application Serial No. PCT/IB2016/052850, filed on 17 May 2016, which claims the benefit of U.S. Provisional Application No. 62/167,384, filed on 28 May 2015. These applications are hereby incorporated by reference herein.

BACKGROUND

1. Field

The present disclosure pertains to an electrode configured to provide electrical contact with skin of a subject.

2. Description of the Related Art

For many applications in the medical field, skin electrodes are used. Electrodes generally provide electrical contact with a subject's skin to transfer electrical signals between the subject's skin and a medical device. Electrodes generally include a conductive layer or material that is used to transmit and receive electrical signals to and from the subject. Electrodes are generally either dry electrodes or wet electrodes.

Wet electrodes rely on an electrolyte material, such as a hydrogel or gel, to provide a conductive path and fill in gaps between the electrode and the skin of the subject. Wet electrodes are generally used for shorter periods of time due to the hydrogel or gel drying out. Wet electrodes may also cause irritation to the skin due to the gel material.

Dry electrodes rely on the natural salt and/or sweat on the skin of the subject to provide a flow path for the electrical signals transmitted to and/or received from the skin of the subject. Dry electrodes may be used for longer periods of time because they do not dry out. Dry electrodes may be difficult to couple to the skin of the subject without gaps and may not stay in place well if a subject moves.

The skin's stratum corneum (i.e., upper layer consisting of dead cells) is a high impedance barrier since it contains limited amount of body fluids with ions. That is, there is minimal, but non-negligible, ionic transfer through the stratum corneum (upper skin layer), which means very weak currents pass through the stratum corneum layer.

The resistance of the stratum corneum layer is highly dependent on the presence and activity of sweat glands and ducts (as well as other pathways such as sebaceous glands, hair follicles and skin imperfections) which secrete fluids containing Na+, K+ and Cl− ions of differing concentrations than extracellular fluid. In case of a dry electrode interface, this is not a very stable electron-electrolyte contact condition. That is, the sweat production may create a local microclimate but with a dry electrode interface this is not a very stable electrical contact.

With regards to dry electrode applications, skin deformation may cause the same artifacts; however, due to the lower levels of skin adhesion, relative sliding of the electrodes may occur in differing degrees depending on the material. As the electrolytic sweat layer accumulates between the skin and the dry electrode, the potential difference across the epidermis increases and the impedance of the electrode falls and settles at a particular value. If the dry electrode is allowed to change position on the skin, the electrode-skin interface would now lack the sweat layer, a motion artifact will be presented, and the impedance of the electrode will be higher until ample time occurs for the electrode-skin interface to stabilize as sweat is formed.

The applications of the skin electrodes use different electrical derivatives of body signals. One is the voltage potential on the skin being used to derive body state information such as Electrocardiogram, ECG (heart-activity) and Electroencephalogram, EEG (brain-activity). Skin impedance is used to measure, for example, stress (Galvanic Skin Response, GSR) or Electrical Impedance Tomography, EIT (lung monitoring). Another application is electrical stimulation of the skin, such as Transcutaneous Electrical Nerve Stimulation, TENS. Skin impedance measurement is used to make sure the stimulation electrode is in good electrical contact with the skin.

In all these applications, it is desired to have low galvanic impedance with the skin in order to have good quality signals. For applications, such as daily sleep monitoring or long-term TENS treatment it is also important to have an easy to use electrode.

Wet or adhesive gel electrodes are known for the low impedance due to the moisture and conductive Ag/AgCl particles. But, the drawbacks of these gel electrodes include single use, limited durability, peel off skin irritation, ease of attachment to body and device, etc. All together it makes the gel electrodes not very suitable for daily long term use at home for medical or consumer health applications. Comfortable dry electrodes resolve most of those issues but hardly achieve the signal quality and low impedance which is achieved with wet or hydrogel electrodes. Therefore, an improved dry electrode with a low impedance skin interface and that can also be easily integrated into consumer medical devices is desired.

SUMMARY

Accordingly, one or more aspects of the present disclosure relate to an electrode that is configured to provide electrical contact with skin of a subject. The electrode includes an electrode body configured to be removably coupled with the skin of the subject and to receive electrical signals from and/or transmit electrical signals to the skin of the subject, and an electrical coupling that facilitates coupling the electrode to an external computing system. The electrode body includes a conductive silicone material configured to enable uptake or diffusion of moisture from the skin of the subject over which the electrode body is disposed; and a detergent configured to facilitate a flow of ions through the conductive silicone material.

Yet another aspect of the present disclosure relates to a method for providing electrical contact with skin of a subject via an electrode. The electrode includes an electrode body and an electrical coupling. The method includes removably coupling, with the electrode body, the electrode with the skin of the subject, the electrode body comprises a conductive silicone material for enabling uptake or diffusion of moisture from the skin of the subject over which the electrode body is disposed and a detergent for facilitating a flow of ions through the conductive silicone material; receiving and/or transmitting electrical signals from and/or to the skin of the subject via the conductive silicone material of the electrode body; and coupling of the electrode to an external computing system.

Still another aspect of present disclosure relates to an electrode that configured to provide electrical contact with the skin of a subject. The electrode includes means for receiving electrical signals from and/or transmitting electrical signals to the skin of the subject, and means for facilitating coupling of the electrode to an external computing system. The means for receiving from and/or transmitting includes a conductive silicone material for enabling uptake or diffusion of moisture from the skin of the subject over which the means for receiving and/or transmitting is disposed and a detergent for facilitating a flow of ions through the conductive silicone material.

These and other objects, features, and characteristics of the present disclosure, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the disclosure.

DETAILED DESCRIPTION OF EXEMPLARY EMBODIMENTS

Figure 1:
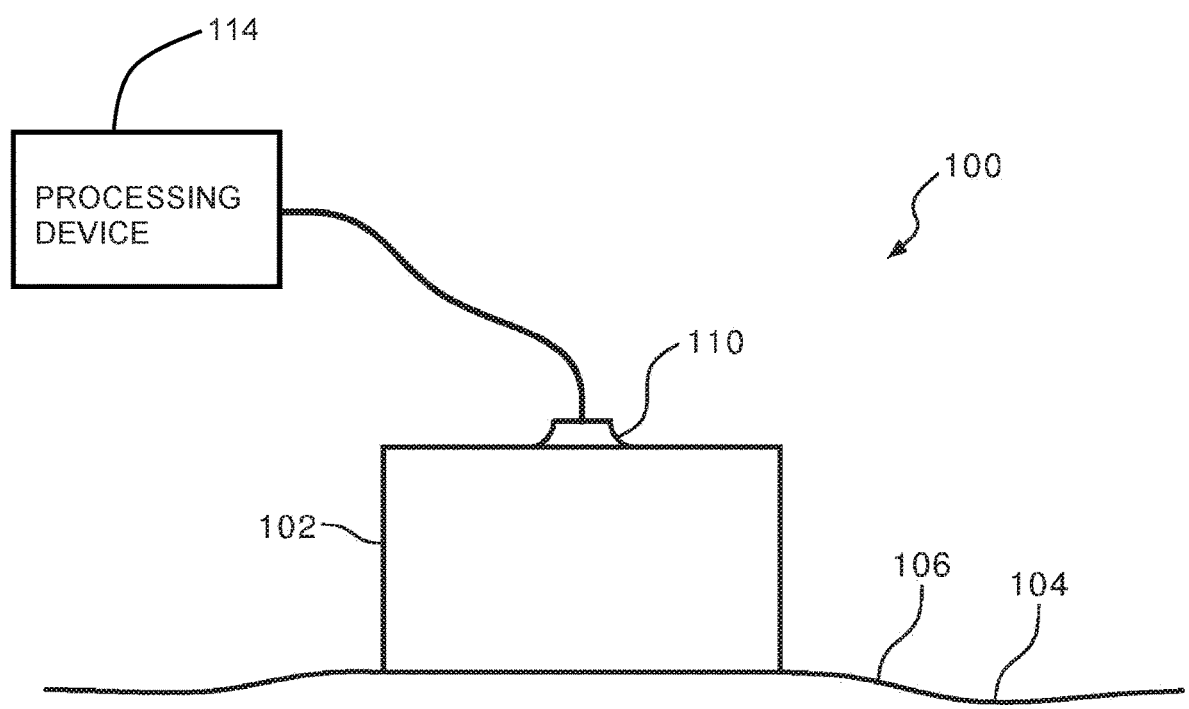
FIG. 1 illustrates an exemplary electrode in accordance with an embodiment of the present patent application.

As used herein, the singular form of "a", "an", and "the" include plural references unless the context clearly dictates otherwise. As used herein, the statement that two or more parts or components are "coupled" shall mean that the parts are joined or operate together either directly or indirectly, i.e., through one or more intermediate parts or components, so long as a link occurs. As used herein, "directly coupled" means that two elements are directly in contact with each other. As used herein, "fixedly coupled" or "fixed" means that two components are coupled so as to move as one while maintaining a constant orientation relative to each other.

As used herein, the word "unitary" means a component is created as a single piece or unit. That is, a component that includes pieces that are created separately and then coupled together as a unit is not a "unitary" component or body. As employed herein, the statement that two or more parts or components "engage" one another shall mean that the parts exert a force against one another either directly or through one or more intermediate parts or components. As employed herein, the term "number" shall mean one or an integer greater than one (i.e., a plurality).

Directional phrases used herein, such as, for example and without limitation, top, bottom, left, right, upper, lower, front, back, and derivatives thereof, relate to the orientation of the elements shown in the drawings and are not limiting upon the claims unless expressly recited therein.

FIG. 1 illustrates an electrode 100 in accordance with an embodiment of the present patent application. Electrode 100 includes an electrode body 102 configured to be removably coupled with the skin 104 of a subject 106 and to receive electrical signals from and/or transmit electrical signals to skin 104 of subject 106, and an electrical coupling 110 that facilitates coupling electrode 100 to an external computing system 114. Electrode body 102 includes a conductive silicone material configured to enable uptake or diffusion of moisture from skin 104 of subject 106 over which electrode body 102 is disposed; and a detergent configured to facilitate a flow of ions through the conductive silicone material. The present patent application provides conductive particles filled dry silicone electrode 100 with detergent additives for optimal sensing electrical contact with skin 104 of subject 106. Electrode 100 is soft and skin friendly due to the hydrophilic silicone material having moisture regulating properties.

In some embodiments, electrode body 102 includes silicone material, electrical conductive particles, and detergent. In some embodiments, the electrical conductive particles may include graphite, carbon or silver flakes or particles. In some embodiments, the electrical conductive particles are mixed with the silicone material to form a conductive silicone material. In some embodiments, electrode body 102 may include a range of about 25 to 75% weight of the silicone material, a range of about 20 to 50% weight of the conductive particles and a range of about 5 to 25% weight of the detergent. In some embodiments, electrode body 102 may include 50% weight of the silicone material, 35% weight of the conductive particles and 15% weight of the detergent. In some embodiments, electrode body 102 may be formed by mixing 15 g of the detergent and 35 g of the conductive particles with 50 g of the silicone material. In some embodiments, the silicone material, the conductive particles and the detergent are mixed using mix-extrusion, high speed mixing process, which is performed at temperature ranges of about 10 to 150° C. In some embodiments, the silicone material, the conductive particles and the detergent are mixed using a high speed mixing or mix extrusion device.

In some embodiments, electrode body 102 includes conductive silicone material and detergent. In some embodiments, electrode body 102 may include a range of about 70 to 95% weight of the conductive silicone material and a range of about 5 to 30% weight of the detergent. In some embodiments, electrode body 102 may be formed by mixing 20 g of the detergent with 80 g of the conductive silicone material. In some embodiments, the conductive silicone material and the detergent are mixed using mix-extrusion, high speed mix process, which is performed at temperature ranges of about 10 to 150° C. In some embodiments, the conductive silicone material and the detergent are mixed using a mix extruder or high speed mixer device.

In some embodiments, additional materials (additives) may be added to facilitate mixing of the conductive silicone material and the detergent and/or mixing the silicone material, the conductive particles and the detergent. In some embodiments, such additional materials may be optional. In some embodiments, such additional materials do not change the impedance of the dry electrode formed from the hydrophilic silicone material and the detergent additives.

In some embodiments, the conductive silicone material is configured to provide moisture regulating properties to electrode 100. In some embodiments, the conductive silicone material is a hydrophilic conductive silicone material or a PolyDiMethylSiloxane material. The added hydrophilic properties of the conductive silicone material cause moisture uptake from the subject's skin and from the air surrounding the subject's skin. Thus, the conductive silicone material of the electrode provides a comfortable layer against the skin. In some embodiments, the conductive silicone material may include electrically conductive liquid silicone rubber. In some embodiments, the conductive silicone material may include commercially available Elastosil® LR 3162 material.

In some embodiments, the soap or detergent may include alpha-olefin sulfonate, soap, Sodium (C14-16) olefin sulfonate, and olefin sulfonate. In some embodiments, the soap or detergent are mixed with the conductive silicone material to form a homogeneous material. In some embodiments, the detergent is not only be mixed with the silicone material, but also chemically bonded onto the backbone of the silicone (e.g., PolyDiMethylSiloxane) material. In some embodiments, the soap or detergent may include a double-bond, cross-link chemical structure. In some embodiments, the silicone material may include a cross-link chemical structure. In some embodiments, the soap or detergent and the conductive silicone material are chemically bonded to each other. In some embodiments, the soap or detergent may include commercially available Bio-Terge® AS-90 Beads. In some embodiments, 9% of detergent (e.g., Bio-Terge® AS-90 Beads) may be added to the conductive silicone material (e.g., Elastosil® LR 3162).

In some embodiments, the detergent is configured to absorb water into the silicone material. In some embodiments, the detergent is configured to absorb more than 20% by weight of water. The interaction of water with the ions (added by the detergent) is configured to function as a salt-bridge. In some embodiments, the interaction of water and/or bodily/body fluids with the ions (added by the detergent) is configured to function as an ion-richer electrolyte-electrode bridge.

In some embodiments, the detergent additives which are mixed into the conductive silicone material are configured to improve the ion flow through the conductive silicone material. This improves the electrode-electrolyte interface of the dry silicone electrode. In some embodiments, the electrode is configured to enable current to pass across the electrode-electrolyte interface. In some embodiments, the detergent added to the silicone material may have either a liquid form or a powder/solid form.

In some embodiments, the silicone material may be filled with conductive particles (carbon, graphite, or silver) to obtain electrical properties. In some embodiments, the conductive particle added to the silicone material may have either a liquid form or a powder/solid form. This makes the material conductive for electrons but not for ions. By adding ions into the conductive silicone material, two properties change in favor of lowering the impedance of the electrode path in interaction with the skin. First, the exchange of ions becomes possible and the modified silicone is configured to absorb/drag water from sweat in contact with the skin. In some embodiments, water uptake is not only from the skin but also from e.g. humidity of air, tap water, humid storage packaging, and/or showering. The absorption of water is configured to work as a salt-bridge. The silicone is in this way modified into a bulk hydrophilic compound or a bulk ionic conductive hydrophilic compound.

In some embodiments, by adding conductive particles (e.g., graphite, carbon or silver flakes or particles) and the soap or detergent additives, better sensing and conduction performance of the electrode may be achieved compared to other electrodes compositions where only conductive particles are mixed in. In some embodiments, the electrical conductive particles (e.g., graphite, carbon or silver particles) and the soap or detergent additives provide a better ionic path into the hydrophilic silicone material.

In some embodiments, the chemical structure of the hydrophilic silicone may be given as follows:

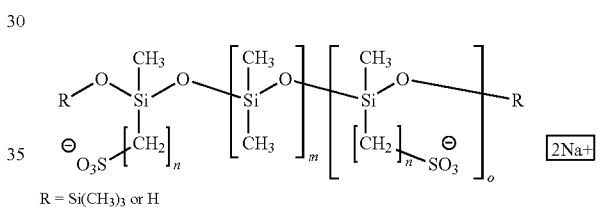

In some embodiments, n in the above chemical structure of the hydrophilic silicone material ranges from 3 to 28. In some embodiments, n ranges from 10 to 18. In some embodiments, n ranges from 12 to 16. In some embodiments, the total number (m+o+1) of repeating units in the above chemical structure of the hydrophilic silicone material may be at least 5 and may be less than 1000, with n and o being integers independently selected from each other and may be at least 6. In some embodiments, the terminal end groups R in the above chemical structure of the hydrophilic silicone material may consist of $Si(CH_3)_3$ and/or hydrogen.

In some embodiments, the synthesis of a hydrophilic silicone material according to this present disclosure may be schematically shown as follows:

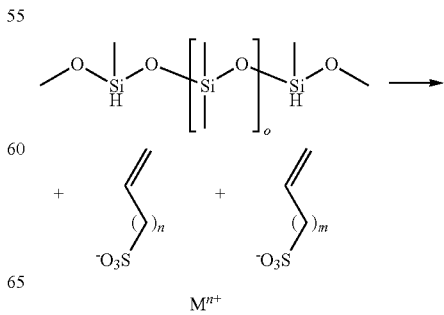

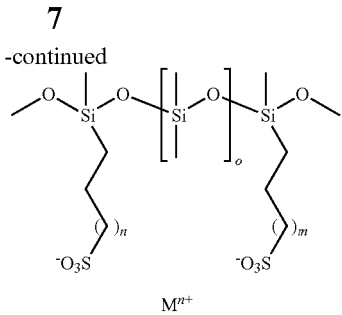

In some embodiments, silicone precursor bearing reactive Si—H group reacts with a hydrophilic monomer such as an alpha-olefin sulfonate. In some embodiments, the value of n and m in the above chemical structure may range from 3 to 28. In some embodiments, the value of n and m may range from 10 to 18. In some embodiments, the value of n and m may range from 12 to 16. In some embodiments, the value of o in the above chemical structure may range from 5 to 1000.

In some embodiments, the olefin component may be strongly hydrophilic because it may include a polar, negatively charged head group ($^-O_3S$) and a cation ($M^{n+}$) for charge balance. In some embodiments, the mixing of the hydrophilic olefin component with the hydrophilic silicone precursor may be hampered by the difference in hydrophilicity. In some embodiments, hydrophilic silicone material according to this present disclosure may include the ion pair composed of the anionic head group and the cationic counter-ion suspended in the hydrophilic matrix of the silicone precursor.

In some embodiments, instead of the silicone material, the electrode may include other polymer compound materials mixed with conductive additives and ion-rich detergent additives. In some embodiments, other alternative detergents that are configured to promote ion flow in the electrode may be used. In some embodiments, other alternative conductive particle/additives that are configured to increase conductivity between the electrode and the subject's skin and to lower impedance of the electrode material may be used.

Electrode 100 includes electrical coupling 110. Electrical coupling 110 facilitates coupling of electrode 100 to external computing system 114. External computing system 114 is a system configured to deliver electrical stimulation to a subject and/or monitor a physiological parameter or such of the subject. In some embodiments, external computing system includes one or more of processing devices (e.g., a digital processor, an analog processor, a digital circuit designed to process information, an analog circuit designed to process information, a state machine, and/or other mechanisms for electronically processing information), one or more sensors, one or more interface devices (e.g., a keypad, buttons, switches, a keyboard, knobs, levers, a display screen, a touch screen, speakers, a microphone, an indicator light, an audible alarm, a printer, a tactile feedback device, and/or other interface devices), and/or other components. In some embodiments, external computing system includes one or more of measurement devices. For example, the one or more of measurement devices may be configured to obtain bioimpedance measurements, biopotential measurements, the electroencephalogram, EEG (brain-activity) measurements, Electrocardiogram, ECG (heart-activity) measurements, Galvanic Skin Response, GSR (stress) measurements, etc.

For example, external computing system 114 may include a bio sensing systems used for electrocardiography (ECG), electroencephalography (EEG), electromyography (EMG), electrooculography (EOG), and/or other bio sensing applications. By way of another example, external computing system 114 may include a bio stimulation system used for transcutaneous electrical nerve stimulation (TENS), electrical muscle stimulation (EMS), neuromuscular electrical stimulation (NMES), functional electrical stimulation (FES), Galvanic Skin Response, GSR (stress), and/or other bio stimulation applications.

Electrical coupling 110 is electrically coupled to electrode body 102 such that it enables electrical signals to be received and/or transmitted from and/or to skin 104 of the subject 106. In some embodiments, additional components and/or layers of material are disposed between electrical coupling 110 and/or electrode body 102. In other embodiments, electrical coupling 110 is directly coupled to electrode body 102. In some embodiments, electrical coupling 110 comprises one or more of a snap assembly, a magnetic assembly, a button assembly, a clip and/or clamp assembly, a wire assembly, and/or other assemblies to facilitate coupling electrode 100 to external computing system 114. For example, electrical coupling 110 includes a portion of a snap assembly for connecting one or more wires from external computing system 114 to electrode 100. In some embodiments, a portion of electrical coupling 110 may be made of a metallic material. In some embodiments, a portion of electrical coupling 110 may be made from the hydrophilic silicone material (with detergent additives).

FIGS. 2-5 illustrate various exemplary configurations of the electrode in accordance with embodiments of the present patent application.

Figure 2:
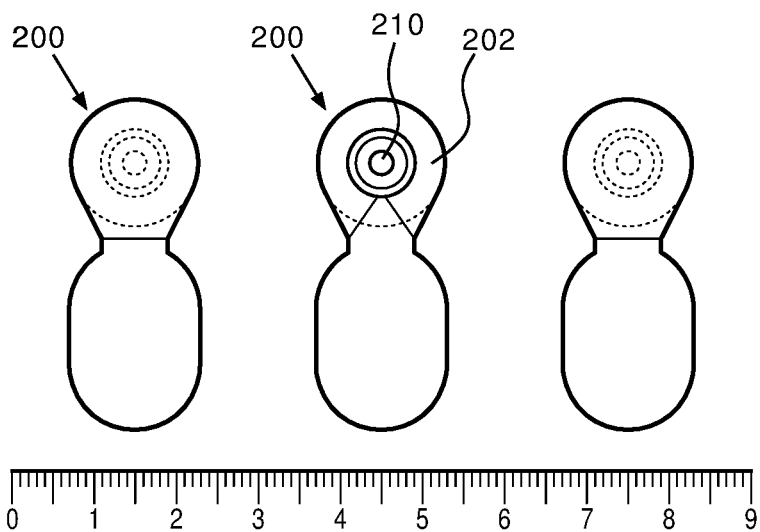
FIGS. 2-5 illustrate various exemplary configurations of the electrode in accordance with embodiments of the present patent application.

Referring to FIG. 2, an electrode 200 may be in the form of a flat electrode with an electrode body 202 and an electrical coupling or snap 210. In some embodiments, electrodes 200 may be used for Electrocardiogram, ECG (heart-activity) measurements.

In some embodiments, hydrophilic silicone material with detergent additives may be in the form of a sheet that a user or an operator has to cut and/or stamp into the desired shape. In some embodiments, hydrophilic silicone material (with detergent additives) sheet may have dimensions of 50 by 50 millimeters. In some embodiments, hydrophilic silicone material (with detergent additives) sheet may have a thickness of 1 millimeter. In some embodiments, the user or operator may laser cut and/or stamp the hydrophilic silicone material (with detergent additives) sheet into the desired shape.

In some embodiments, electrical coupling 210 may be a male portion of a snap and a corresponding female portion of a snap may be coupled to one or more wires configured to couple electrode 200 to external computing system 114. In some embodiments, electrical coupling or snap 210 is pierced through the hydrophilic silicone material (with detergent additives) to establish sufficient mechanical as well as electrical contact.

Figure 3:
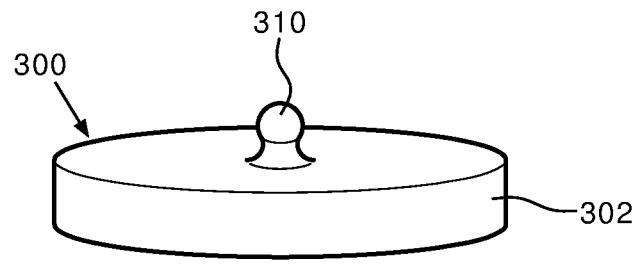

Referring to FIG. 3, electrode 300 may be in the form of a flat electrode with an electrode body 302 and an electrical coupling or snap 310. That is, electrode 300 may be flat shaped electrode with snap protrusion 310. In some embodiments, snap 310 may be centrally positioned on electrode 300.

Figure 4:
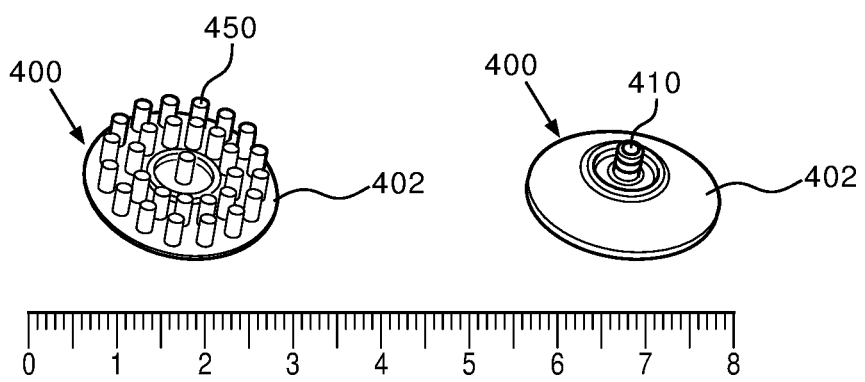

Referring to FIG. 4, electrode 400 may be in the form of a structured pin electrode with an electrode body 402 and an electrical coupling or snap 410. In some embodiments, structured pin electrode 400 may be used, for example, for through-hair measurements. In some embodiments, structured pin electrode 400 may include multi-pin (e.g., pin 450) design that enables electrode 400 to penetrate the hair of the subject in order to establish a good galvanic contact with the skin of the subject. In some embodiments, electrode 400 may have a diameter of 25 millimeters. In some embodiments, pin 450 of electrode 400 may have a height of 5 millimeters. In some embodiments, pin 450 of electrode 400 may have a diameter of 2 millimeters.

Figure 5:
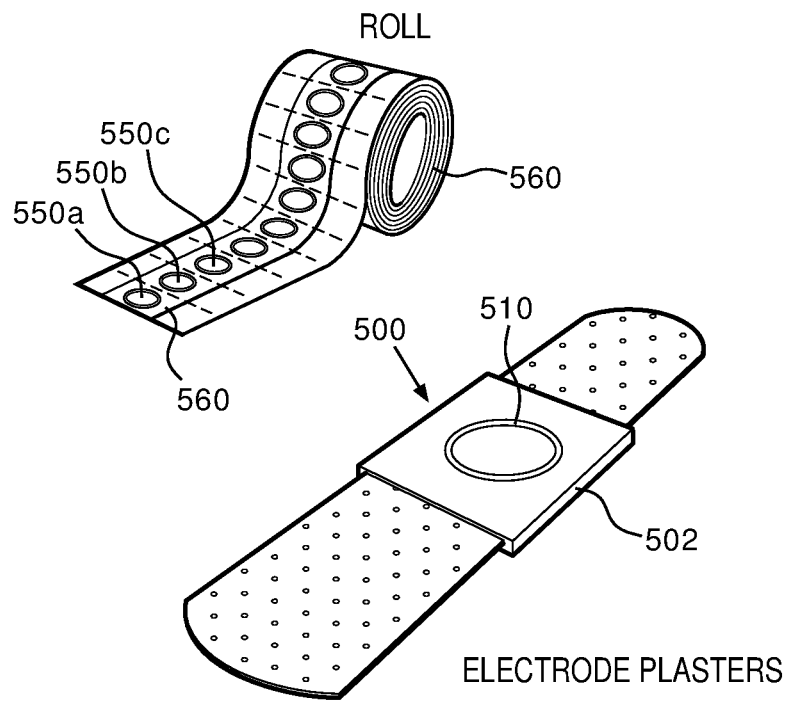

Referring to FIG. 5, electrode 500 may be in the form of a plaster electrode 500 with an electrode body 502 and an electrical coupling 510.

In some embodiments, electrode 550 may be in the form of a strip of electrodes 550a, 550b, 550c, etc. wound into a roll 560. In some embodiments, each of electrodes 550a, 550b, 550c, etc. may include an electrode body and an electrical coupling. In some embodiments, the strip of electrodes may be rolled and stored in a dispenser device. In some embodiments, each of the electrodes 550a, 550b, 550c, etc. may be separated from the other electrode(s) by separating portions (e.g., notches, perforating lines). For example, a user, using the notches or the perforating lines, may separate the strip into individual electrodes 550a, 550b, 550c, etc. for use.

In some embodiments, electrode of the present disclosure may include adhesive members or materials to cause electrode to adhere to the skin of the subject. In some embodiments, adhesive material may be disposed on a rear or a back surface of electrode. In some embodiments, electrode may be used with different adhesive material types. For example, the adhesive for electrode may include skin adhesive material. In some embodiments, the adhesive for electrode may include hydrocolloid or skin friendly silicone adhesive material.

Figure 6:
FIG. 6 illustrates two exemplary configurations of an electrical coupling of the electrode in accordance with embodiments of the present patent application.

FIG. 6 illustrates two exemplary configurations of electrical coupling 110 of electrode 100 in accordance with embodiments of the present patent application. In some embodiments, different connection to leads may be integrated into electrode 100. For example, the left side of FIG. 6 illustrates a portion of a snap assembly 625 for connecting one or more wires from external computing system 114 to electrode 100, while the right side of FIG. 6 illustrates a portion of a snap to magnetic adapter 635 for connecting one or more wires from external computing system 114 to electrode 100. In some embodiments, easy to use magnetic connections may be integrated into electrode 100.

Figure 7:
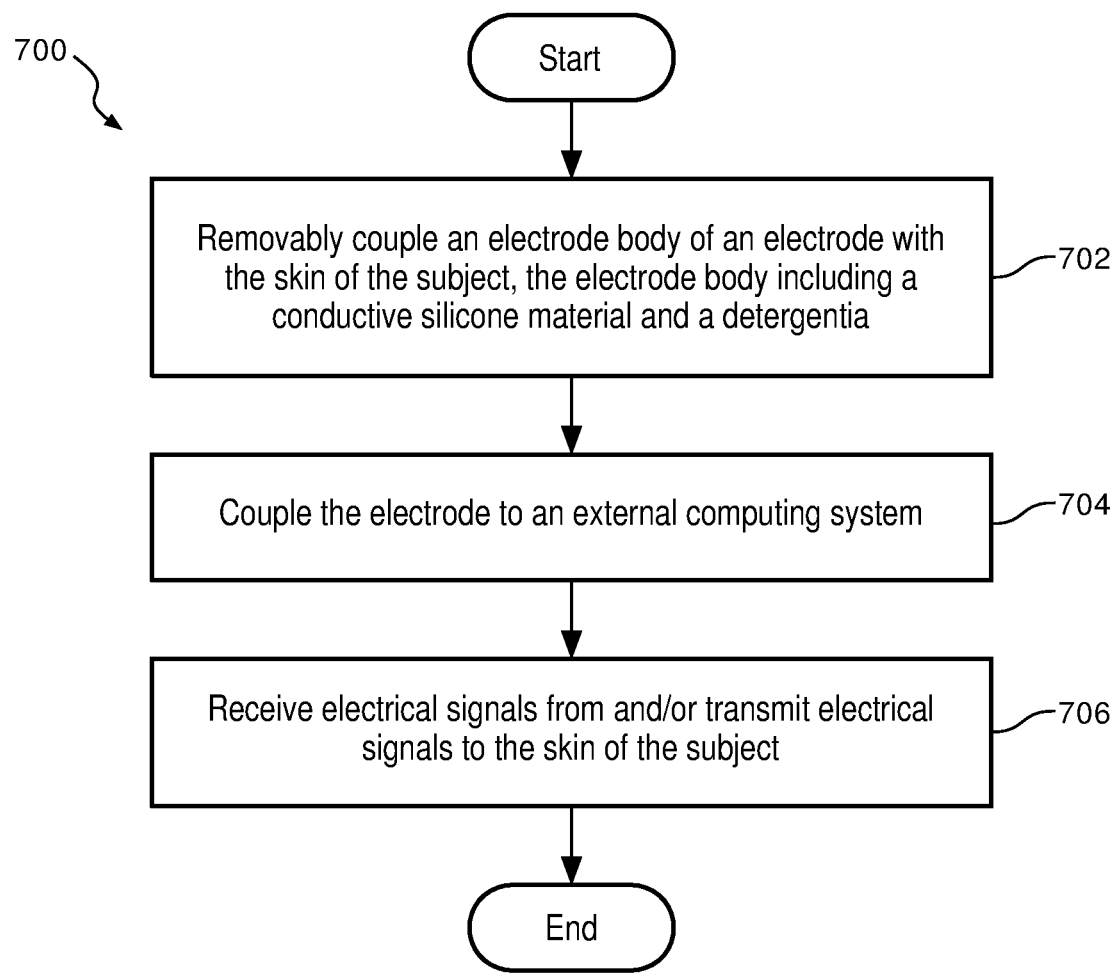
FIG. 7 illustrates a method for providing electrical contact with skin of a subject via an exemplary electrode in accordance with an embodiment of the present patent application.

FIG. 7 illustrates a method 700 for providing electrical contact with skin of a subject via an electrode. The electrode includes an electrode body, an electrical coupling, and/or other components. In some embodiments, more than one electrode may be used. The procedures of method 700 presented herein are intended to be illustrative. In some embodiments, method 700 may be accomplished with one or more additional procedures not described, and/or without one or more of the procedures discussed. Additionally, the order in which the procedures of method 700 are illustrated in FIG. 7 and described herein is not intended to be limiting.

At a procedure 702 of method 700, the electrode body of electrode is coupled with the skin of the subject. Procedure 702 is performed by an electrode body the same as or similar to electrode body 102 (as shown and described with respect to FIG. 1). The electrode body includes a conductive silicone material configured to enable uptake or diffusion of moisture from the skin of the subject over which the electrode body is disposed; and a detergent configured to facilitate a flow of ions through the conductive silicone material. In some embodiments, the conductive silicone material is the same as or similar to the conductive silicone material (as described with respect to FIG. 1). In some embodiments, the detergent is the same as or similar to the detergent (as described with respect to FIG. 1).

At a procedure 704 of method 700, coupling of the electrode is coupled to an external computing system. In some embodiments, coupling of the electrode to an external computing system is facilitated via an electrical coupling the same as or similar to electrical coupling 110 (as shown and described with respect to FIG. 1).

At a procedure 706 of method 700, electrical signals are received and/or transmitted from and/or to the skin of the subject via the electrode body of the electrode. In some embodiments, procedure 706 is performed by an electrode body the same as or similar to electrode body 102 and an electrode the same as or similar to electrode 100 (as shown and described with respect to FIG. 1).

The electrode of the present disclosure may be used on portable medical devices that patients may take home. Other applications of the electrodes of the present disclosure may include other galvanic skin electrode applications such as bio-impedance, Electrocardiogram, ECG (heart-activity), Electroencephalogram, EEG (brain-activity), Electrical Impedance Tomography, EIT (lung monitoring), Transcutaneous Electrical Nerve Stimulation, TENS, Galvanic Skin Response, GSR (stress), etc. In some embodiments, the electrode may be a conductive skin interface that may be used for bioimpedance measurements, biopotential measurements and/or electrical stimulation.

In some embodiments, the electrode of the present disclosure may be used for enhancing sleep. A daily sleep monitoring and enhancing device may be used by problem sleepers on a daily basis. Electrodes with good signal quality, and that provide comfort and ease of use are desirable for the daily sleep monitoring and enhancing device. The daily sleep monitoring and enhancing device may be an advanced closed-loop device which may conveniently monitor the electroencephalogram (EEG) measurement data during sleep and deliver auditory stimulation to induce slow waves. The daily sleep monitoring and enhancing device may include a headset worn during sleep (i.e., the headgear), dry skin electrodes of the present disclosure, a bio-signal (EEG) amplifier and a wireless audio device. The dry electrodes used in the daily sleep monitoring and enhancing device provide ease of use and comfort to the user while providing good EEG signal quality. That is, the dry electrodes of the present disclosure have low galvanic impedance with the skin in order to provide good quality EEG signals.

The dry silicone electrode of the present patent application has been evaluated in a number of electrode applications for galvanic skin sensing, including, Electrocardiogram, ECG (heart-activity), Electroencephalogram, EEG (brain-activity), Galvanic Skin Response, GSR (stress), etc.

Figure 8:
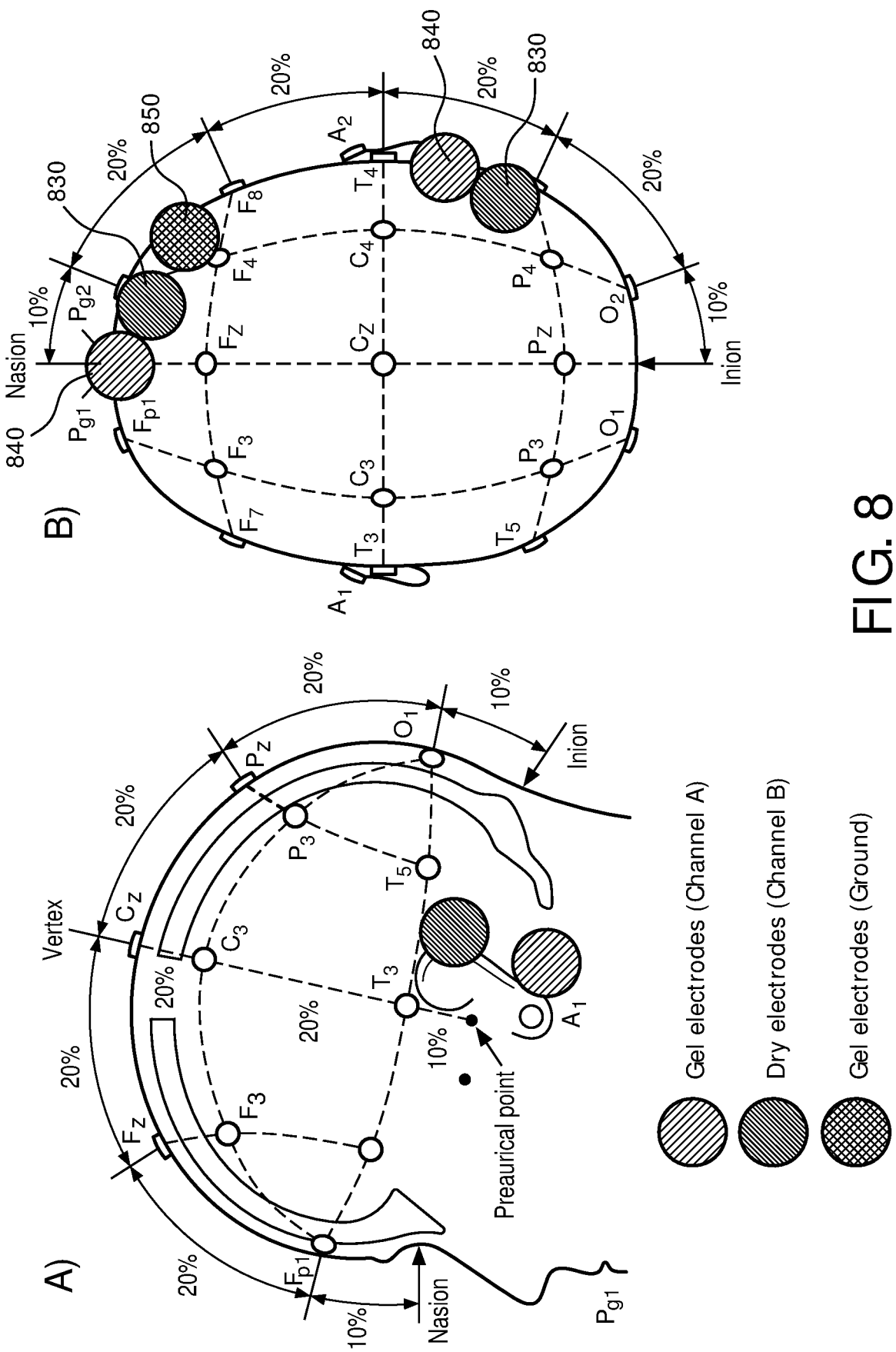
FIGS. 8 and 9 illustrate configurations, locations and fixation of electrodes being used for Electroencephalogram, EEG measurements in accordance with an embodiment of the present patent application.
Figure 9:
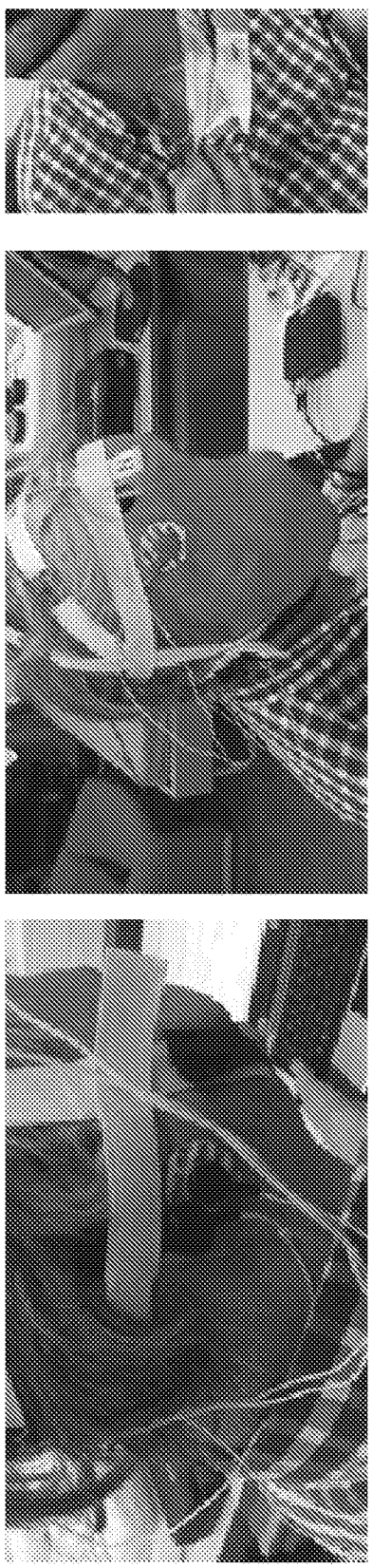

For example, referring to FIGS. 8-11, the dry silicone electrode of the present patent application has been evaluated in an Electroencephalogram, EEG (brain-activity) application in which a comparison of dry silicone electrodes 830 of the present patent application has been made with gel based electrodes 840. Both dry silicone electrodes 830 and gel based electrodes 840 were placed on frontal and behind the ears locations of the subject's head. FIGS. 8 and 9 illustrate configurations, locations and fixation of dry silicone electrodes 830 and gel based electrodes 840 being used for the EEG measurements. The EEG measurement data from dry silicone electrodes 830 and gel based electrodes 840 were simultaneous recorded. For example, the EEG measurement data from dry silicone electrodes 830 was recorded on channel B and the EEG measurement data from gel based electrodes 840 was recorded on channel A, respectively. A common grounding electrode 850 was also used during the EEG measurement procedure. The EEG measurements have been conducted using a TMSI Nexus 10 system. Dry silicone electrodes 830 may include snap interconnect member for electrical coupling(s). In some embodiments, the snap interconnect member may be a metallic snap interconnect member (insulated from the skin).

Eight subjects have been measured. Per subject, three recordings have been done. One recording includes a repetition of three periods of eyes closed followed by a period of eyes open. Two recordings use thirty second periods and the third recording uses sixty seconds period. The two recordings of the thirty second periods are used as cross check. Results were reported using the sixty second periods. The performance indicators of the EEG measurement data are signal comparison in time domain (e.g., alpha waves); power spectrum overlap in 0.5-30 Hz window for eyes closed, and power spectrum overlap in 0.5-30 Hz window for eyes open.

Figure 10:
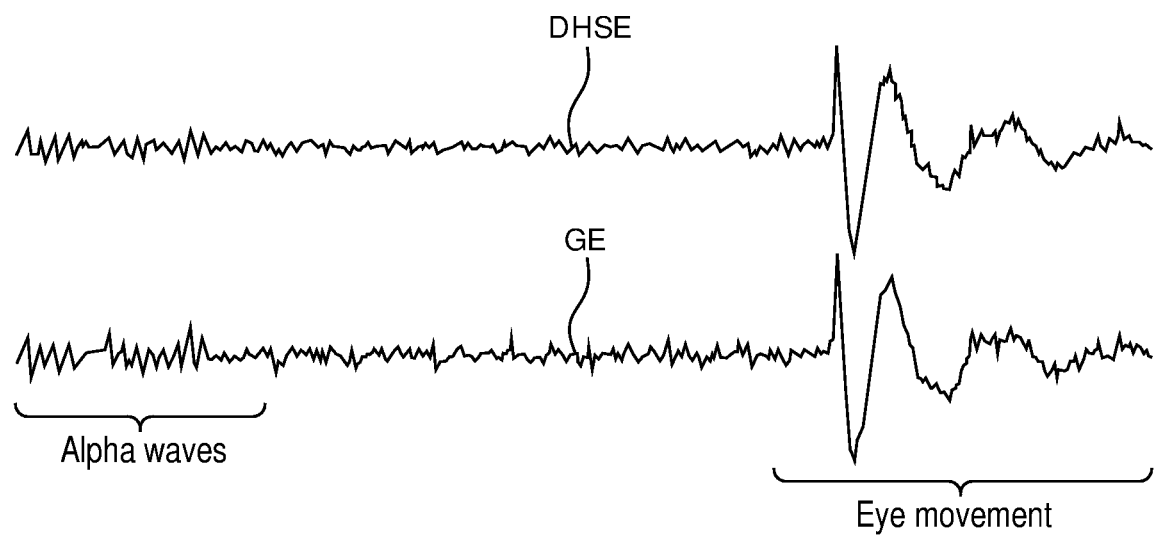
FIGS. 10 and 11 illustrate a comparison and an overlay of EEG measurement data obtained from hydrogel electrodes and dry electrodes in accordance with an embodiment of the present patent application.
Figure 11:
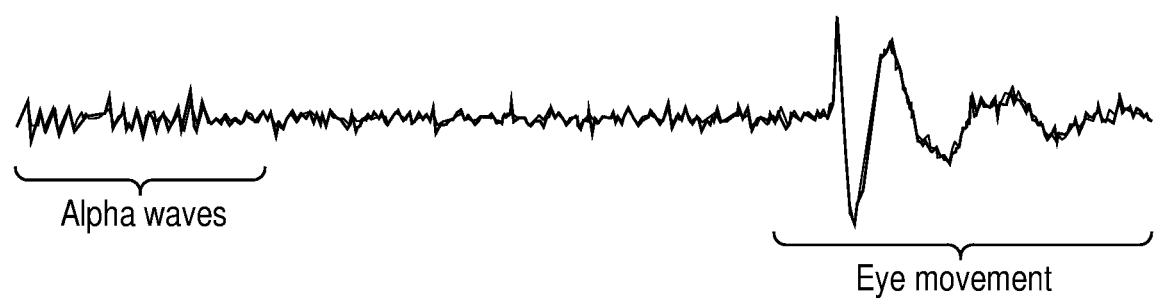

FIGS. 10 and 11 illustrate a comparison and an overlay of EEG measurement data obtained from hydrogel electrodes 840 and dry silicone electrodes 830. A ten second section of the EEG measurements, as shown in FIGS. 10 and 11, includes clear alpha waves in the first seconds and includes large eye motion artifacts (eye movement) at the end of the measurement data. Signal, DSE shows the dry silicone electrode signal and Signal, GE represents the gel electrode signal. In FIG. 11, the signals DSE and GE are overlayed to show the similarities and differences therebetween. Both, alpha waves as well as large eye motion artifacts show very comparable results between data obtained from hydrogel electrodes 840 and dry silicone electrodes 830.

The experiments/tests provide evidence that the performance of the dry silicone electrodes of the present patent application is comparable to that of wet and gel electrodes. The experimental data was compared and benchmarked with the standard of wet and gel electrodes, which are known for the good signal quality (but also have their own drawbacks as discussed above). The experimental data indicated that the dry silicone electrodes of the present patent application with the hydrophilic conductive silicone material and detergent additives resolves those issues maintaining good signal quality.

The results of these experiments also indicated that a high level of overlap (and therewith similar electrode characteristic) of gel and dry silicone electrodes is present. The results of these experiments also indicated that motion artifacts for dry electrodes are present in similar amount and appearance as for gel electrodes.

Water uptake experiments and weight loss experiments were also conducted and the results of these experiments indicated that the electrode material (hydrophilic conductive silicone with detergent additives) of the present patent application does not dry out, for example, in a period of time (e.g., a few months). Further, the results of these experiments indicated that the electrode of the present patent application provides good signal quality even after months of storing them openly in an office environment. Also, during volunteer tests (where there was a few day interval between the tests), the same electrodes were re-used and no special packaging requirements were used for the electrodes. This provides further evidence that the electrodes of the present patent application do not dry out or degrade over days of use.

In some embodiments, additional ions, provided by the detergent, are available for charge transfer within the hydrophilic silicone material of the electrode body and improved conduction performance of the electrode. In some embodiments, the effect of hydrophilicity is introduced to the silicone material by the detergent additives. Good performance of the dry hydrophilic silicone electrodes of the present patent application may further be explained by the enhanced ion transfer compared to other dry electrode materials.

Figure 12:
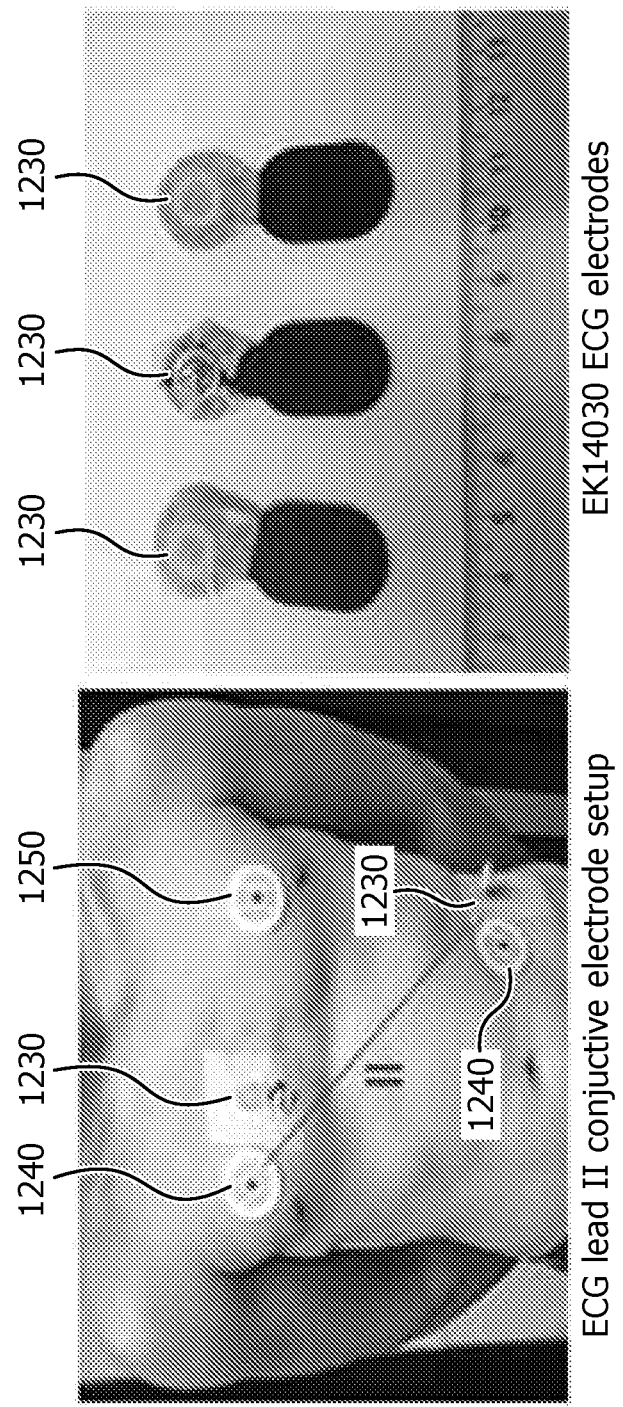
FIG. 12 illustrates dry electrodes being used for Electrocardiogram, ECG measurements and their locations in accordance with an embodiment of the present patent application.

Referring to FIGS. 12-15, the dry silicone electrode of the present patent application has also been evaluated in an Electrocardiogram, ECG (heart-activity) application in which a comparison of dry silicone electrodes 1230 of the present patent application has been made with gel based electrodes 1240. The right hand side image of FIG. 12 illustrates dry silicone electrodes 1230, while the left hand side image of FIG. 12 illustrates gel based electrodes 1240 and dry silicone electrodes 1230 being used for the ECG measurements. A common grounding electrode 1250 was also used during the ECG measurement procedure. The common grounding electrode 1250 was positioned on the left breast. The ECG measurement data from dry silicone electrodes 1230 and gel based electrodes 1240 were simultaneous recorded. A three lead configuration was used for ECG measurements, with a first channel for dry silicone electrodes 1230, a second channel for gel based electrodes 1240, and a third channel for common grounding electrode 1250. For example, the ECG measurement data from dry silicone electrodes 1230 was recorded on one channel and the ECG measurement data from gel based electrodes 1240 was recorded on the second channel. The ECG measurements have been conducted using a TMSI Nexus 10 system. Dry silicone electrodes 1230 were made using EK14030.

Dry silicone electrodes 1230 may include a thickness of 1 millimeter and a geometric configuration having dimensions of 18 by 50 by 1 millimeters. Dry silicone electrodes 1230 may include snap interconnect member for electrical coupling(s). In some embodiments, the snap interconnect member may be a metallic snap interconnect member (insulated from the skin).

Four subjects have been measured for about fifteen minutes with repeating periods of rest (sitting), sit-ups and walking on the spot. After a generic third order 1 Hz high pass filter, the ECG data signals from dry silicone electrodes 1230 and gel based electrodes 1240 appear very similar. ECG characteristic peaks P, Q, R, S, T were visible in both wet electrodes 1240 and dry silicone electrodes 1230. Motion artifacts were observed for both electrode types, especially during intended motion periods.

Figure 13:
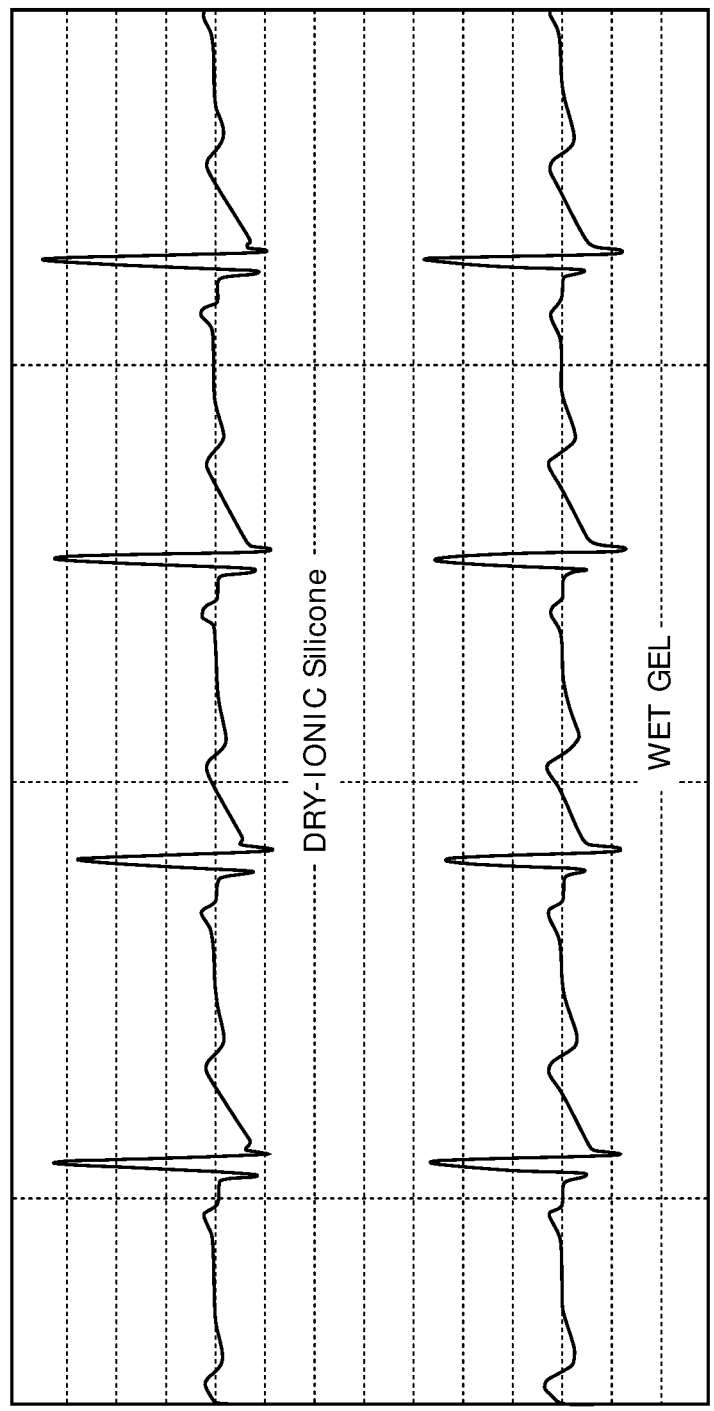
FIGS. 13-15 illustrate comparisons of ECG measurement data obtained from hydrogel electrodes and dry electrodes in accordance with an embodiment of the present patent application.
Figure 14:
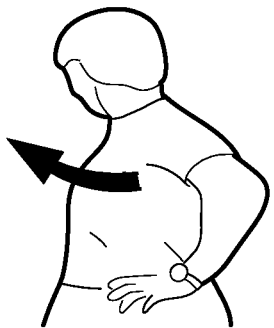
Figure 14:
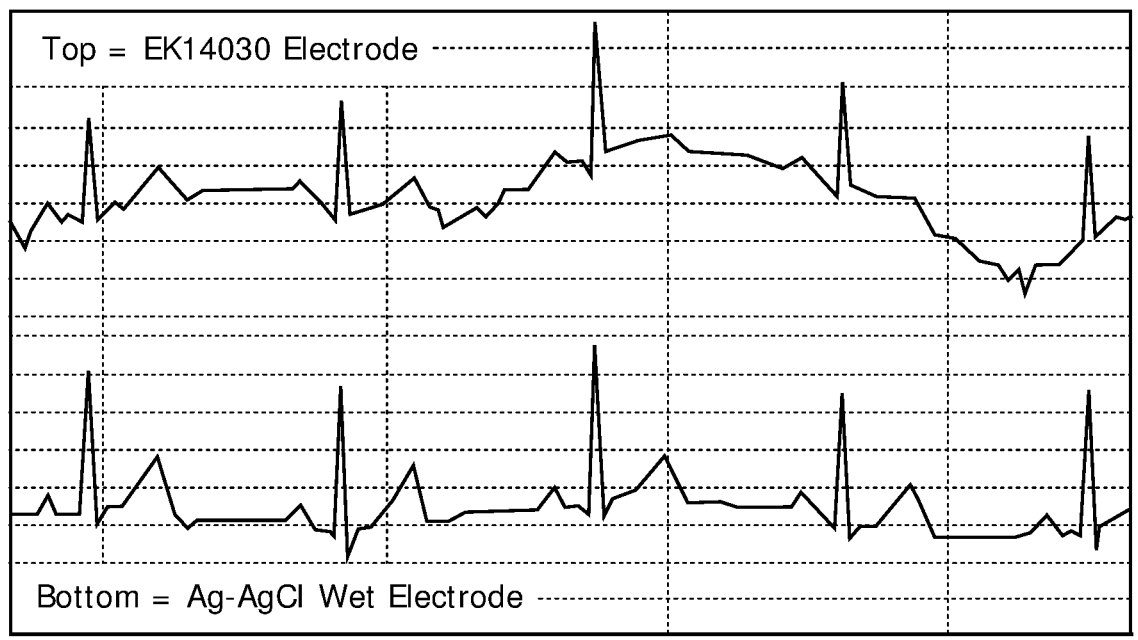
Figure 15:
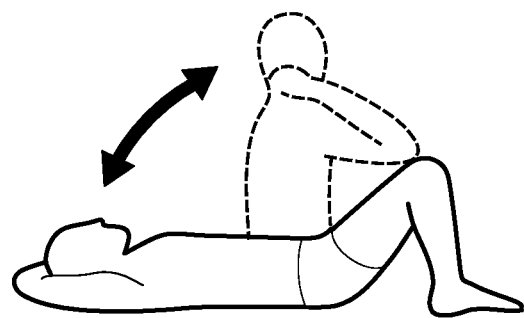
Figure 15:
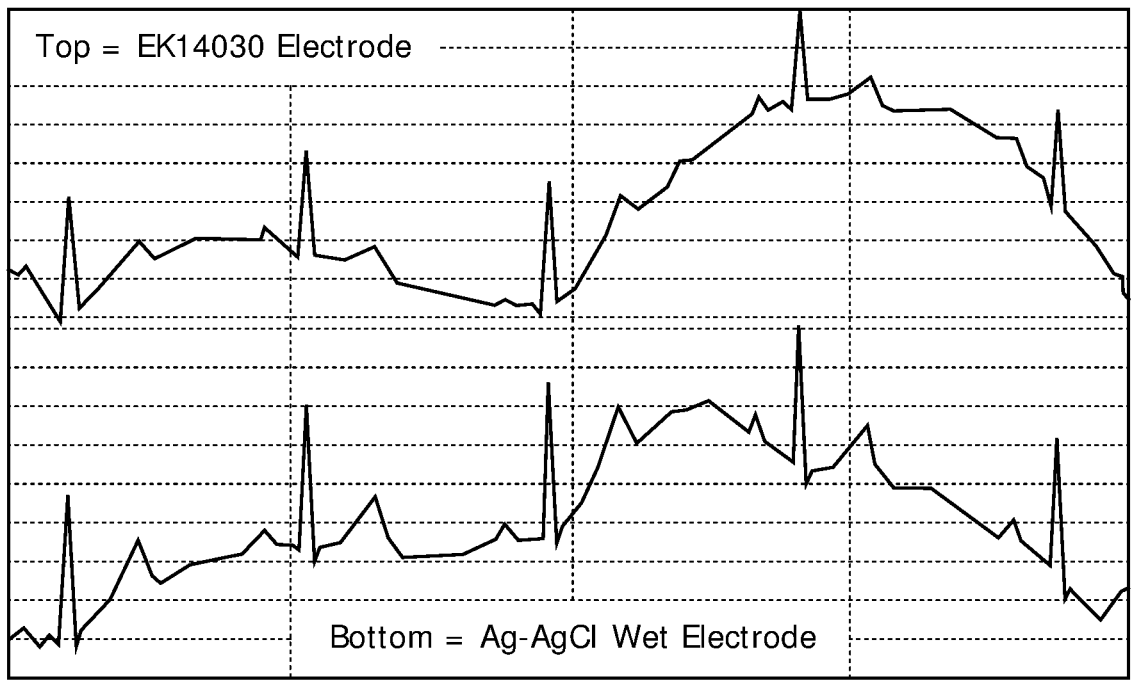

FIGS. 13-15 illustrate comparisons of ECG measurement data obtained from hydrogel electrodes 1240 and dry silicone electrodes 1230. FIG. 13 illustrates ECG snapshots (e.g., five seconds) from wet/gel electrodes 1240 and dry silicone electrodes 1230 when the subjects were at a rest position (i.e., sitting on a chair). FIG. 14 illustrates ECG data from wet/gel electrodes 1240 and dry silicone electrodes 1230 when the subjects were performing a torso rotation (as shown in FIG. 14). FIG. 15 illustrates ECG snapshots (e.g., five seconds) for wet/gel electrodes 1240 and dry silicone electrodes 1230 when subjects were performing an up and down movement (as shown in FIG. 15).

In the context of the various embodiments of the present patent application, hydrophilic materials are hydrophilic silicones, with a crosslinking structure and/or crosslinking density comparable to that of suitable hydrophobic materials. Hydrophilic silicones have a normal silicone backbone but instead of hydrophobic methyl or phenyl groups some of these groups are exchanged for more hydrophilic side groups. Hydrophilic side groups may contain, for example, alcohol, carboxylic acid, amine, amide and ethylene glycol functional groups.

In the claims, any reference signs placed between parentheses shall not be construed as limiting the claim. The word "comprising" or "including" does not exclude the presence of elements or steps other than those listed in a claim. In a device claim enumerating several means, several of these means may be embodied by one and the same item of hardware. The word "a" or "an" preceding an element does not exclude the presence of a plurality of such elements. In any device claim enumerating several means, several of these means may be embodied by one and the same item of hardware. The mere fact that certain elements are recited in mutually different dependent claims does not indicate that these elements cannot be used in combination.

Although the description provided above provides detail for the purpose of illustration based on what is currently considered to be the most practical and preferred embodiments, it is to be understood that such detail is solely for that purpose and that the disclosure is not limited to the expressly disclosed embodiments, but, on the contrary, is intended to cover modifications and equivalent arrangements that are within the spirit and scope of the appended claims. For example, it is to be understood that the present disclosure contemplates that, to the extent possible, one or more features of any embodiment can be combined with one or more features of any other embodiment.

What is claimed is:

1. An electrode configured to provide electrical contact with skin of a subject, the electrode comprising:
   (a) an electrode body comprising (i) a conductive silicone material comprising (i) PolyDiMethylSiloxane, (ii) electrical conductive particles and (iii) a detergent configured to facilitate a flow of ions through the conductive silicone material; and
   (b) an electrical coupling coupled to the electrode body that facilitates coupling of the electrode to an external computing system.

2. The electrode of claim 1, wherein the detergent comprises olefin sulfonate.

3. The electrode of claim 1, wherein the detergent is about 5% to 30% by weight of the electrode body.

4. The electrode of claim 1, wherein the detergent is configured to chemically bond with the conductive silicone material.

5. The electrode of claim 1, wherein the electrical conductive particles comprise graphite, carbon or silver flakes.

6. The electrode of claim 1, wherein the electrical conductive particles are about 20 to 50% by weight of the electrode body.

7. The electrode of claim 1, wherein the PolyDiMethylSiloxane is about 25 to 75% by weight of the electrode body.

8. The electrode of claim 1, wherein the electrode body comprises 25 to 75% by weight PolyDiMethylSiloxane, 20 to 50% by weight electrical conductive particles and 5 to 25% by weight detergent.

9. The electrode of claim 1, wherein the electrode body comprises 50% by weight PolyDiMethylSiloxane, 35% by weight electrical conductive particles and 15% by weight detergent.

10. The electrode of claim 1, wherein the electrode body is configured to enable uptake or diffusion of moisture from the skin of a subject and to receive electrical signals from or transmit electrical signals to the skin of the subject.

11. The electrode of claim 1, wherein the conductive silicone material is configured to enable uptake or diffusion of moisture from the skin of the subject over which the electrode body is disposed.

12. The electrode of claim 11, wherein the detergent is configured to provide ions into the conductive silicone material, and wherein an interaction of the moisture and the ions provides a salt-bridge in the electrode that allows the flow of ions through the conductive silicone material.

13. The electrode of claim 1, wherein the electrical conductive particles comprise graphite powder, carbon powder or silver powder.

14. The electrode of claim 1, wherein the electrical coupling is configured to deliver electrical stimulation to the subject and/or monitor a physiological parameter of the subject.

15. The electrode of claim 14, wherein the electrical coupling is configured to obtain one or more of bioimpedance measurements, biopotential measurements, an electroencephalogram (EEG), EEG measurements, an electrocardiogram (ECG), ECG measurements, galvanic skin response (GSR), and GSR stress measurements.

16. The electrode of claim 1, wherein the electrical coupling comprises one or more of a snap coupling, a magnetic coupling, a button coupling, a clip coupling, a clamp coupling, and a wire coupling.

17. The electrode of claim 1, wherein the electrical coupling comprises a structured multi-pin electrode.

18. The electrode of claim 1, wherein the electrical coupling comprises a separating portion wherein the electrical coupling is removed from a strip of electrical couplings.

19. A system configured to deliver electrical stimulation to a subject and/or monitor a physiological parameter of the subject, the system comprising:
   an external computing system configured to deliver the electrical stimulation to the subject and/or monitor a physiological parameter of the subject; and
   an electrode configured to provide electrical contact with skin of the subject, the electrode comprising:
   (a) an electrode body comprising (i) a conductive silicone material comprising (i) PolyDiMethylSiloxane, (ii) electrical conductive particles and (iii) a detergent configured to facilitate a flow of ions through the conductive silicone material, and
   (b) an electrical coupling coupled to the electrode body and to the external computing system.

20. The system of claim 19, wherein the conductive silicone material is configured to enable uptake or diffusion of moisture from the skin of the subject over which the electrode body is disposed.

21. The system of claim 19, wherein the electrical conductive particles comprise graphite powder, carbon powder or silver powder.

* * * * *